United States Patent
Schurter et al.

[11] Patent Number: 4,875,923
[45] Date of Patent: Oct. 24, 1989

[54] N-PYRIDINYLSULFONYL-N'-PYRIMIDINY-LUREAS

[75] Inventors: Rolf Schurter, Binningen; Willy Meyer; Werner Föry, both of Riehen, all of Switzerland

[73] Assignee: Ciba-Geigy Corporation, Ardsley, N.Y.

[21] Appl. No.: 114,993

[22] Filed: Oct. 26, 1987

Related U.S. Application Data

[63] Continuation-in-part of Ser. No. 719,614, Apr. 3, 1985.

[30] Foreign Application Priority Data

Apr. 11, 1984 [CH] Switzerland .................. 1822/84

[51] Int. Cl.$^4$ .................... C07D 401/12; A01N 43/54
[52] U.S. Cl. ......................... 71/92; 544/321; 544/324; 544/331
[58] Field of Search ............. 71/92; 544/321, 324, 544/331

[56] References Cited

U.S. PATENT DOCUMENTS 4,668,279  5/1987  Rorer ........................ 71/90

FOREIGN PATENT DOCUMENTS 0071441  2/1983  European Pat. Off.
0096593  12/1983  European Pat. Off.
3105453  10/1982  Fed. Rep. of Germany.
3225471  1/1984  Fed. Rep. of Germany.
580608  10/1976  Switzerland.

OTHER PUBLICATIONS

Chemical Abstracts 99, 53793m (1983).

Primary Examiner—John M. Ford
Attorney, Agent, or Firm—Kevin T. Mansfield; Edward McC. Roberts

[57] ABSTRACT

N-Pyridinylsulfonyl-N'-pyrimidinylureas and N-pyridinylsulfonyl-N'-triazinylureas of the formula

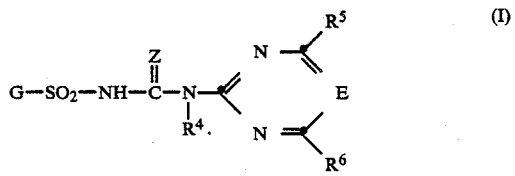

wherein
E is nitrogen or the methine bridge,
Z is oxygen or sulfur,
$R^4$ is hydrogen or $C_1$-$C_4$alkyl,
$R^5$ and $R^6$ are each independently hydrogen, halogen, $C_1$-$C_4$alkyl, $C_1$-$C_4$haloalkyl, $C_1$-$C_4$alkoxy, $C_1$-$C_4$haloalkoxy, $C_2$-$C_4$-alkylthio, $C_3$-$C_6$cycloalkyl or —$NR^{12}R^{13}$,
G is a

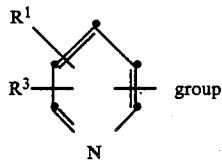

group $R^1$ is hydrogen, halogen, nitro, $C_1$-$C_4$alkyl, $C_1$-$C_4$alkoxy, trifluoromethyl, trifluoromethoxy, difluoromethoxy, $C_1$-$C_4$alkyl carbonyl or —$COOR^{14}$,
$R^3$ is a

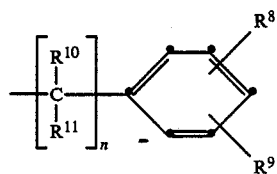

group,
n is 0, 1 or 2,
$R^8$ is hydrogen, $C_1$-$C_4$alkyl, $C_1$-$C_4$alkoxy, halogen, $C_1$-$C_4$haloalkyl, nitro, —$COOR^{14}$, $C_1$-$C_4$haloalkoxy, —O—$CR^{15}R^{16}$—CN,
$R^9$ is hydrogen, halogen, $C_1$-$C_4$alkyl, $C_1$-$C_4$alkoxy, $C_2$-$C_4$alkoxyalkyl oder $C_2$-$C_4$alkoxylkoxy,
$R^{10}$ and $R^{11}$ are each independently hydrogen or $C_1$-$C_4$alkyl,
$R^{12}$ and $R^{13}$ are each independently hydrogen or $C_1$-$C_4$alkyl,
$R^{14}$ is hydrogen, $C_1$-$C_4$alkyl, $C_2$-$C_4$alkenyl, $C_3$-$C_4$alkynyl, or is $C_1$-$C_4$alkyl which is substituted by $C_1$-$C_4$alkoxy, halogen or phenyl, and
$R^{15}$ and $R^{16}$ are each independently hydrogen or $C_1$-$C_4$alkyl, and the salts thereof have useful selective herbicidal properties for controlling weeds in crops of useful plants.

14 Claims, No Drawings

N-PYRIDINYLSULFONYL-N'-PYRIMIDINYLUREAS

CROSS REFERENCE TO RELATED APPLICATIONS

This a a continuation-in-part of application Ser. No. 719,614 pending filed on Apr. 3, 1985.

The present invention relates to novel sulfonylureas with herbicidal and plant growth regulalting properties, to the preparation thereof, to compositions containing them as active ingredients, and to methods of using them for controlling weeds, preferably selectively, in crops of useful plants, or for regulating and inhibiting plant growth. The invention further relates to novel sulfonamides prepared as intermediates and to derivatives thereof.

The invention relates to sulfonylureas of the formula I

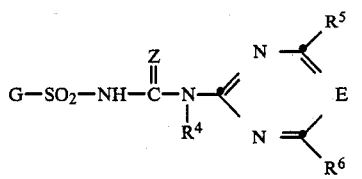

wherein
E is nitrogen or the methine bridge,
Z is oxygen or sulfur,
$R^4$ is hydrogen or $C_1$-$C_4$alkyl,
$R^5$ and $R^6$ are each independently hydrogen, halogen, $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_3$-$C_6$dialkoxyalkyl, $C_1$-$C_4$haloalkylthio, $C_2$-$C_4$-alkoxyalkyl, $C_3$-$C_6$cycloalkyl or —$NR^{12}R^{13}$,
G is a

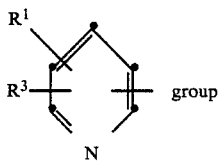

group, $R^1$ is hydrogen, halogen, nitro, $C_1$-$C_4$-alkyl, $C_1$-$C_4$alkoxy, trifluoromethyl, trifluoromethoxy, difluoromethoxy, $C_1$-$C_4$alkylcarbonyl or —$COOR^{14}$,
$R^3$ is a

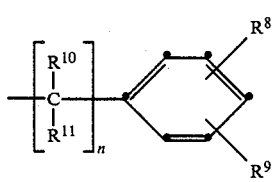

group, n is 0, 1 or 2,
$R^8$ is hydrogen, $C_1$-$C_4$alkyl, $C_1$-$C_4$alkoxy, halogen, $C_1$-$C_4$haloalkyl, nitro, —$COOR^{14}$, $C_1$-$C_4$haloalkoxy, —O—$CR^{15}R^{16}$—$COOR^{14}$ or —O—$CR^{15}R^{16}$—CN,
$R^9$ is hydrogen, halogen, $C_1$-$C_4$alkyl, $C_1$-$C_4$alkoxy, $C_2$-$C_4$alkoxyalkyl oder $C_2$-$C_4$alkoxyalkoxy, $R^{10}$ and $R^{11}$ are each independently hydrogen or $C_1$-$C_4$alkyl,
$R^{12}$ and $R^{13}$ are each independently hydrogen or $C_1$-$C_4$alkyl,
$R^{14}$ is hydrogen, $C_1$-$C_4$alkyl, $C_2$-$C_4$alkenyl, $C_3$-$C_4$alkynyl, or is $C_1$-$C_4$alkyl which is substituted by $C_1$-$C_4$alkoxy, halogen or phenyl, and
$R^{15}$ and $R^{16}$ are each independently hydrogen or $C_1$-$C_4$alkyl, and to the salts thereof.

Ureas, triazines and pyrimidines with herbicidal properties are generally known in the art. Sulfonylureas with herbicidal and plant growth regulating action have recently been described, for example in published European patent application Nos. 39 239, 41 404, 45 196, 57 456, 64 804 and 70 698.

In the above definitions, alkyl denotes straight chain or branched alkyl, e.g. methyl, ethyl, n-propyl, isopropyl, or the four butyl isomers.

Alkoxy denotes methoxy, ethoxy, n-propyloxy, isopropyloxy, or the four butyloxy isomers, with methoxy, ethoxy or isopropyloxy being preferred.

Alkylthio is e.g. methylthio, ethylthio, n-propylthio, isopropylthio, or the four butylthio isomers, with methylthio and ethylthio being preferred.

Cycloalkyl is generally cyclopropyl, cyclobutyl, cyclopentyl or cyclohexyl.

Halogen itself or as moiety of a substituent such as haloalkoxy, haloalkylthio or haloalkyl is fluorine, chlorine and bromine, with fluorine and chlorine being preferred. Haloalkyl itself or as moiety of haloalkoxy or haloalkylthio is normally chloromethyl, fluoromethyl, difluoromethyl, trifluoromethyl, 2-chloroethyl, 2,2,2-trifluoroethyl, 1,1,2,2-tetrafluoroethyl, pentafluoroethyl, 1,1,2-trifluoro-2-chloroethyl, 2,2,2-trifluoro-1,1-dichloroethyl, pentachloroethyl, 3,3,3-trifluoropropyl, 2,3-dichloropropyl, 1,1,2,3,3,3-hexafluoropropyl, with fluoromethyl, chloromethyl, difluoromethyl and trifluoromethyl being preferred.

Alkoxyalkyl is e.g. methoxymethyl, methoxyethyl, methoxypropyl, ethoxyethyl, ethoxymethyl or propyloxymethyl. Alkoxyalkoxy is e.g. methoxymethoxy, methoxyethoxy, methoxypropyloxy, ethoxymethoxy, ethoxyethoxy and propyloxymethoxy. Within the scope of the present invention, dialkoxyalkyl will generally be understood as meaning the following radicals: dimethoxymethyl, 2,2-dimethoxyethyl, 1,2-dimethoxyethyl, 1,2-diethoxyethyl, 2,2-diethoxyethyl, 2,2-dimethoxypropyl, 3,3-dimethoxypropyl, 1,1-dimethoxyethyl, 1,1-diethoxyethyl, 1,1-dimethoxypropyl, 2,3-dimethoxypropyl, 1,1-dimethoxybutyl, 2,2-dimethoxybutyl, 3,3-dimethoxybutyl, 4,4-dimethoxybutyl, with the geminal dialkoxyalkyl radicals, which may also be designated as acetals, being preferred.

Alkenyl radicals are vinyl, allyl, 2-butenyl, 3-butenyl or methallyl. Alkynyl is propargyl, 2-butyl or 3-butynyl. Allyl and propargyl are preferred.

Alkylcarbonyl radicals are in particular acetyl, propionyl, butyryl, isobutyryl, valeryl, isovaleryl or pivaloyl.

The invention also comprises the salts which the compounds of formula I are able to form with amines, alkali metal bases and alkaline earth metal bases, or with quaternary ammonium bases.

Preferred salt-forming alkali metal hydroxides and alkaline earth metal hydroxides are the hydroxides of lithium, sodium, potassium, magnesium or calcium, most preferably those of sodium or potassium.

Examples of suitable salt-forming amines are primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline. Preferred amine are ethylamine, propylamine, diethylamine or triethylamine, with isopropylamine, diethanolamine and 1,4-diazabicyclo[2.2.2]octane being most preferred.

Examples of quaternary ammonium bases are, in general, the cations of haloammonium salts, e.g. the tetramethylammonium cation, the tetraethylammonium cation, the trimethylethylammonium cation, and also the ammonium cation.

Among the compounds of formula I, those compounds are preferred wherein either (a) Z is oxygen or (b) $R^1$ is hydrogen, Cl, F, $CH_3$, $C_2H_5$, $CH_3O$, $CF_3$, $CH_3CO$ or (c) $R^5$ and $R^6$ together contain not more than 4 carbon atoms and $R^4$ is hydrogen or (d) G is 3-phenylpyridin-2-yl.

A further preferred subgroup of compounds of formula I comprises those compounds wherein Z is oxygen, $R^4$ is hydrogen and G is 3-phenylpyridin-2-yl and $R_5$ and $R_6$ together contain not more than 4 carbon atoms.

A preferred individual compound of formula I is:

N-(3-phenylpyridin-2-ylsulfonyl)-N'-(4,6-dimethoxypyrimidin-2-yl)urea.

The preparation of the compounds of formula I is generally carried out by the following methods.

In accordance with a first process, the compounds of formula I are obtained by reacting a substituted sulfonamide of formula II

G—SO$_2$—NH$_2$ (II)

wherein G is as defined for formula I, with a carbamate of formula III

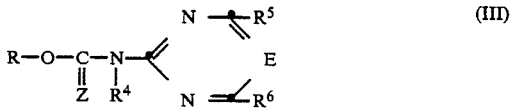

(III)

wherein E, $R^4$, $R^5$, $R^6$ and Z are as defined for formula I and R is phenyl, alkyl or substituted phenyl, in the presence of a base.

In accordance with a second process, the compounds of formula I are obtained by reacting a sulfonylcarbamate of formula IV

G—SO$_2$—NH—C—O—R (IV)
                    ‖
                    Z wherein G and Z are as defined for formula I and R is phenyl, alkyl or substituted phenyl, with an amine of formula V

(V)

wherein E, $R^4$, $R^5$ and $R^6$ are as defined for formula I.

Finally, the compounds of formula I can also be obtained by reacting a sulfonylisocyanate of formula VI

G—SO$_2$—N=C=Z (VI)

wherein G and Z are as defined for formula I, with an amine of formula V above.

If desired, the resultant ureas of formula I can be converted into addition salts with amines, alkali metal hydroxides or alkaline earth metal hydroxides or with quaternary ammonium bases. This is accomplished e.g. by reaction with the equimolar amount of base and by evaporating off the solvent.

It is convenient to carry out these reactions for obtaining compounds of formula I in aprotic, inert organic solvents. Examples of such solvents are hydrocarbons such as benzene, toluene, xylene or cyclohexane, carbon tetrachloride, or chlorobenzene; ethers such as diethyl ether, ethylene glycol dimethyl ether, diethylene glycol dimethyl ether, tetrahydrofuran or dioxane; nitriles such as acetonitrile or propionitrile; amides such as dimethylformamide, diethylformamide or N-methylpyrrolidinone. The reaction temperatures are preferably in the range from −20° C. to +120° C. The coupling reactions are normally slightly exothermic and can be carried out at room temperature. To shorten the reaction time or also to initiate the reaction, it is expedient to heat the reaction mixture briefly to boiling point. The reaction times can also be shortened by addition of a few drops of a base as catalyst. Preferred bases are tertiary amines such as trimethylamine, triethylamine, quinuclidine, 1,4-diazabicyclo[2.2.2]octane, 1,5-diazabicyclo[4.3.0]non-5-ene or 1,8-diazabicyclo[5.4.0]undec-7-ene. However, the bases employed may also be inorganic bases, e.g. hydrides such as sodium hydride or calcium hydride, hydroxides such as sodium hydroxide or potassium hydroxide, carbonates such as sodium carbonate or potassium carbonate, or bicarbonates such as potassium bicarbonate or sodium bicarbonate.

The final products of formula I can be isolated by concentrating and/or evaporating off the solvent and purified by recrystallising or triturating the solid residue in solvents in which they are not readily soluble, e.g. an ether, an aromatic hydrocarbon or a chlorinated hydrocarbon.

The intermediates of formulas II, IV and VII are novel. They have been specially develolped for the synthesis of compounds of formula I and therefore constitute a further object of the present invention.

The intermediates of formula II are prepared by processes known per se. Thus, for example, the compounds of formula II are obtained by diazotising an amine of formula VII

G—NH$_2$ (VII)

wherein G is as defined for formula I, in hydrochloric acid, and reacting the diazo group with sulfur dioxide in the presence of a catalyst such as copper chloride and reacting the resultant sulfonyl chloride of formula VIII

G—SO$_2$—Cl (VIII)

wherein G is as defined for formula I, with ammonia. The corresponding starting amines are known or they can be obtained by known processes, e.g. by reduction from the corresponding nitro compounds. Further, the compounds of formula II can be obtained by converting a sulfonic acid of formula IX $$G-SO_2-OH \quad (IX)$$

wherein G is as defined for formula I, by treatment with a chlorinating agent such as PCl$_5$, POCl$_3$, COCl$_2$ or SOCl$_2$, to give the corresponding sulfonyl chloride of formula VIII and reacting said chloride with ammonia.

Likewise, the compounds of formula II can be obtained by treating a benzyl thioether of formula X $$G-S-CH_2-C_6H_5 \quad (X)$$

wherein G is as defined for formula I, with chlorine and reacting the resultant sulfonyl chloride of formula VIII with ammonia.

In some cases the sulfonyl chlorides of formula VIII are obtained by direct sulfochlorination of the substituted compound of formula XI $$G-H \quad (XI)$$

wherein G is as defined for formula I, with chlorosulfonic acid ClSO$_3$H.

The pyridinylsulfonylisocyanates of formula VI can be obtained e.g. by phosgenating the sulfonamides of formula II, in the presence of butyl isocyanate and in an inert solvent, at reflux temperature. Similar reactions are described in "Neuere Methoden der präparativen organischen Chemie", Band VI, 211–229, Verlag Chemie, Weinheim, 1970.

The isothiocyanates of formula VI are obtained by treating the sulfonamides of formula II with carbon disulfide and potassium hydroxide and subsequently phosgenating the dipotassium salt. Such processes are described in Arch. Pharm. 229, 174 (1966).

The pyridinylsulfonylcarbamates of formula IV are obtained by reacting the sulfonamides of formula II with a carbonate in the presence of a base. Similar processes are described in Japanese patent specification No. 61 169.

The starting aminopyrimidines and aminotriazines of formula V and corresponding carbamates of formula III are either known or they can be prepared by known methods from compounds disclosed in the literature.

The compounds of formulae VII, VIII, IX, X and XI are known or can be prepared by methods analogous to known ones.

The compounds of formula I are stable compounds and no precautionary measures are required for handling them.

When used at low rates of application, the compounds of formula I have good selective growth inhibiting and selective herbicidal properties which make them most suitable for use in crops of useful plants, preferably in cereals, cotton, soybeans and maize, and most preferably in rice. In some cases damage is also caused to weeds which have only been controlled up to now with total herbicides.

The mode of action of these compounds is unusual. Many are translocatable, i.e. they are absorbed by the plant and transported to other parts of it where they then exert their action. Thus, for example, it is possible to damage perennial weeds to the roots by surface treatment. Compared with other herbicides and growth regulators, the novel compounds of formula I are effective even when used at very low rates of application.

The compounds of formula I have in addition pronounced growth regulating, especially growth inhibiting, properties. The growth of both monocots and dicots is inhibited.

Thus, for example, the compounds of formula I selectively inhibit the growth of leguminosae which are frequently planted as cover crops in tropical regions, so that, while soil erosion between cultivated plants is prevented, the cover crops cannot compete with the cultivated plants.

Inhibition of the vegetative growth of many cultivated plants permits more plants to be sown in a crop area, so that a higher yield may be obtained per unit of area. A further mechanism of yield increase using growth regulators resides in the fact that nutrients are able increasingly to promote flower formation and fruiting, whereas vegetative growth is inhibited.

At higher rates of application of compounds of formula I, all tested plants are so severely damaged in their development that they die.

The invention also relates to herbicidal and growth regulating compositions which contain a novel compound of formula I, and also to methods of controlling weeds pre- and postemergence and of inhibiting the growth of monocots and dicots, especially grasses, tropical cover crops and tobacco plant suckers.

The compounds of formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of applications, such as spraying, atomising, dusting, scattering or pouring, are chosen in accordance with the intended objectives and the prevailing circumstances.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$-$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzene sulfonic acid, dibutylnaphthalenesulfonic acid, or of a naphthalenesulfonic acid/formaldehyde condensation product.

Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 10 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, such as polyoxyethylene sorbitan trioleate, are also suitable non-ionic surfactants.

Cationic surfactants are preferably quaternary ammonium salts which contain, as N-substituent, at least one $C_8$-$C_{22}$alkyl radical and, as further substituents, unsubstituted or halogenated lower alkyl, benzyl or hydroxylower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications:

"McCutcheon's Detergents and Emulsifiers Annual", MC Publishing Corp., Ridgewood, N.J., 1981; H. Stache, "Tensid-Taschenbuch", 2nd Edition, C. Hanser Verlag, Munich & Vienna, 1981; M. and J. Ash, "Encyclopedia of Surfactants", Vol. I–III, Chemical Publishing Co., New York, 1980–81.

The herbicidal compositions usually contain 0.1 to 95%, preferably 0.1 to 80%, of a compound of formula I, 1 to 99%, of a solid or liquid adjuvant, and 0 to 25%, preferably 0.1 to 25%, of a surfactant.

Preferred formulations are composed in particular of the following constituents (%=percentage by weight):

| | |
|---|---|
| Emulsifiable concentrates | |
| active ingredient | 1 to 20%, preferably 5 to 10% |
| surfactant | 5 to 30%, preferably 10 to 20% |
| liquid carrier | 50 to 94%, preferably 70 to 85% |
| Dusts | |
| active ingredient | 0.1 to 10%, preferably 0.1 to 1% |
| solid carrier | 99.9 to 90%, preferably 99.9 to 99% |
| Suspension concentrates | |
| active ingredient | 5 to 75%, preferably 10 to 50% |
| water | 94 to 24%, preferably 88 to 30% |
| surfactant | 1 to 40%, preferably 2 to 30% |
| Wettable powders | |
| active ingredient | 0.5 to 90%, preferably 1 to 80% |
| surfactant | 0.5 to 20%, preferably 1 to 15% |
| solid carrier | 5 to 95%, preferably 15 to 90% |
| Granulates | |
| active ingredient | 0.5 to 30%, preferably 3 to 15% |
| solid carrier | 99.5 to 70%, preferably 97 to 85% |

Whereas commercial products will be preferably formulated as concentrates, the end user will normally employ dilute formulations. The formulations can be diluted to a concentration as low as 0.001% of active ingredient. The rates of application are normally from 0.01 to 10 kg a.i./ha, preferably from 0.025 to 5 kg a.i./ha.

The compositions may also contain further ingredients such as stabilisers, antifoams, viscosity regulators, binders, tackifiers, as well as fertilisers and other compounds for obtaining special effects.

PREPARATORY EXAMPLES

EXAMPLE P1

N-(3-Phenylpyridin-2-ylsulfonyl)-N'-(4,6-dimethoxypyrimidin-2-yl) urea (a) 2-Benzylthio-3-phenyl-pyridine 24.7 g of benzylmercaptane are solved in 450 ml of dimethylformamide and treated with 27.7 g of potassium carbonate. To the resulting mixture 37.9 g of 2-chloro-3-phenyl-pyridine are added dropwise. The mixture is heated to +80° C. for 20 hours, and then poured into ice-water. The aqueous mixture is extracted twice with ethyl acetate. The combined extracts are washed with water and brine, dried over magnesium sulfate, and concentrated. The resulting slurry is treated with petrol ether and the crystalline precipitate is separate, yielding 34.7 g of 2-benzylthio-3-phenyl-pyridine, melting at 99°–100° C.

(b) 3-Phenyl-pyridin-2-ylsulfonamide 15.4 g of 2-benzylthio-3-phenyl-pyridine are suspended in a mixture of 135 ml of 36% hydrochloric acid and 33 ml of water. This suspension is cooled to a temperature between −5° C. and −10° C. and 14.7 g of gaseous chlorine are introduced at this temperature. The mixture is worked up by extracting the reaction mixture with methylene chloride. The organic extracts are washed with water and brine, dried over magnesium sulfate and concentrated. The residue is solved in 150 ml of tetrahydrofurane and cooled to a temperature between −10° C. and −15° C. Gaseous ammonia is blown onto the surface of the solution until the pH-value of the solution is above 10. The mixture is agitated for a further 16 hours and then concentrated. The residue is taken up with a mixture of ethyl acetate and water and acidified by addition by hydrochloric acid. The organic phase is separated and the aqueous phase extracted once with ethyl acetate. The combined organic phases are washed with water and brine, dried over magnesium sulfate and concentrated. Recrystallising the residue from a ethyl acetate/petrolether-mixture yields 10,6 g of 3-phenylpyridin-2-ylsulfonamide, melting at 172° C.

(c) 1.9 g of 3-phenyl-pyridin-2-ylsulfonylsulfonamide and 2.2 g of N-(4,6-dimethoxy-pyrimidin-2-yl)-phenyl-carbamat are dispersed in 40 ml of acetonitrile. A solution of 1.2 ml 1,8-diazabicyclo[5.4.0]undec-7-ene in 5 ml of acetonitrile are added dropwise, whereby a clear solution is obtained. This reaction solution is kept at room temperature for 16 hours. Then 0.7 ml of methanesulfonic acid and subsequently 15 ml of ice-water are added. A colourless percipitate is formed, which is collected, washed with water and dried. The separated precipitate is treated with ether and dried, yielding 3.2 g of N-(3-phenyl-pyridin-2-ylsulfonyl)-N′-(4,6-dimethoxypyrimidin-2-yl) urea, having a melting point of 181° C. with decomposition.

The intermediates and final products listed in the following tables are prepared in analogous manner.

TABLE 1

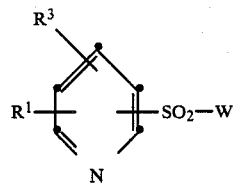

| Comp. | W | Position −SO$_2$−W | R$^1$ | R$^3$ | physical data |
|---|---|---|---|---|---|
| 1.01 | NH$_2$ | 2 | H | 3-phenyl | m.p. 172° C. |
| 1.02 | NH$_2$ | 2 | H | 3-benzyl | |
| 1.03 | NH$_2$ | 2 | 5-Cl | 3-phenyl | |
| 1.04 | NH$_2$ | 3 | 2-Cl | 6-phenyl | |
| 1.05 | Cl | 3 | H | 2-phenyl | |
| 1.06 | Cl | 3 | 5-Cl | 2-phenyl | |

TABLE 2

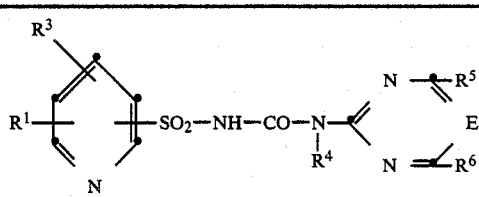

| Comp. | Position −SO$_2$− | R$^1$ | R$^3$ | R$^4$ | R$^5$ | R$^6$ | E | physical data |
|---|---|---|---|---|---|---|---|---|
| 2.01 | 2 | H | 3-phenyl | H | OCH$_3$ | OCH$_3$ | CH | m.p. 181° C. (decomp.) |
| 2.02 | 2 | H | 3-phenyl | H | OCH$_3$ | OCH$_3$ | N | |
| 2.03 | 2 | H | 3-phenyl | CH$_3$ | OCH$_3$ | OCH$_3$ | CH | |
| 2.04 | 2 | H | 3-benzyl | H | OCH$_3$ | OCH$_3$ | CH | |
| 2.05 | 2 | 5-Cl | 3-phenyl | H | OCH$_3$ | OCH$_3$ | CH | |
| 2.06 | 2 | 5-Cl | 3-phenyl | H | OCH$_3$ | OCH$_3$ | N | |
| 2.07 | 3 | 2-Cl | 6-phenyl | H | OCH$_3$ | OCH$_3$ | CH | |
| 2.08 | 3 | H | 2-phenyl | H | CH$_3$ | OCH$_3$ | CH | |
| 2.09 | 3 | H | 2-phenyl | H | CH$_3$ | OCH$_3$ | N | |

FORMULATION EXAMPLES

EXAMPLE F1

Formulation Examples for compounds of formula I (percentages are by weight)

| (a) Wettable powders | (a) | (b) | (c) |
|---|---|---|---|
| compound of formula I | 20% | 50% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7—8 moles of ethylene oxide) | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspension of the desired concentration.

| (b) Emulsifiable concentrate | (a) | (b) |
|---|---|---|
| compound of formula I | 10% | 1% |
| octylphenol polyethylene glycol ether (4-5 moles of ethylene oxide) | 3% | 3% |
| calcium dodecylbenzenesulfonate | 3% | 3% |
| castor oil polyglycol ether | | |

-continued

| (b) Emulsifiable concentrate | (a) | (b) |
|---|---|---|
| (36 moles of ethylene oxide) | 4% | 4% |
| cyclohexanone | 30% | 10% |
| xylene mixture | 50% | 79% | emulsions of any required concentration can be obtained from this concentrate by dilution with water.

| (c) Dusts | (a) | (b) |
|---|---|---|
| compound of formula I | 0.1% | 1% |
| talcum | 99.9% | — |
| kaolin | — | 99% |

Dusts which are ready for use are obtained by mixing the active ingredient with the carriers, and grinding the mixture in a suitable mill.

| (d) Extruder granulate | (a) | (b) |
|---|---|---|
| compound of formula I | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| compound of formula I | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| compound of formula I | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| compound of formula I | 5% |
| isopropylamine | 1% |
| octylphenol polyethylene glycol ether (78 moles of ethylene oxide) | 3% |
| water | 91% |

BIOLOGICAL EXAMPLES

EXAMPLE B1

Preemergence herbicidal action

Plastic pots are filled with expanded vermiculite (density: 0.135 g/cm$^3$, water-absorbing capacity: 0.565 l/l). After the non-adsorptive vermiculite has been saturated with an aqueous emulsion in deionised water which contains the test compound in a concentration of 70.8 ppm, seeds of the following plants are sown on the surface: *Nasturtium officinalis, Agrostis tenuis, Stellaria media* and *Digitaria sanguinalis*. The pots are then kept in a climatic chamber at 20° C., an illumination of about 20 klux and a relative humidity of 70%. During the germinating phase of 4 to 5 days, the pots are covered with lightpermeable material and watered with deionised water to increase the local humidity. After the 5th day, 0.5% of a commercial liquid fertiliser (Greenzit ®, ex Ciba-Geigy) is added to the water. The test is evaluated 12 days after sowing and the action on the plants is assessed.

In this test the compounds of formula I show strong herbicidal activity.

EXAMPLE B2

Growth inhibition of tropical leguminous cover crops

The test plants (*Centrosema plumieri* and *Centrosema pubescens*) are reared until fully grown and then cut back to a height of 60 cm. The plants are sprayed 7 days later with an aqueous emulsion of the test compound. The test plants are kept at 70% relative humidity and 600 lux artificial light for 14 hours per day, at day temperatures of 27° C. and night temperatures of 21° C. The test is evaluated 4 weeks after application by assessing and weighing the new growth compared with controls and by determining the phytotoxicity.

In this test a marked reduction in new growth of the plants treated with compounds of the formula I is observed (less than 20% of the new growth of untreated control plants), without damage being caused to the test plants.

EXAMPLE B3

Growth regulation of soybeans

Soybeans of the "Hark" variety are sown in plastic containers in an earth/peat/sand mixture (6:3:1). The containers are put into a climatic chamber and the plants develop to the 5–6 trefoil leaf stage after about 5 weeks by optimum control of temperature, light, fertiliser addition, and watering. The plants are then sprayed with an aqueous mixture of a compound of formula I until thoroughly wetted. The concentration corresponds to up to 100 g a.i. per hectare. Evaluation is made about 5 weeks after application. Compared with untreated controls, the compounds of formula I markedly increase the number and weight of the harvested siliquae on the leading shoot.

EXAMPLE B4

Growth inhibition of cereals

Summer barley (*Hordeum vulgare*) and summer rye (*Secale*) are sown in sterilised soil in plastic beakers in a greenhouse and watered as required. The cereal shoots are treated about 21 days after sowing with an aqueous spray mixture of a compound of the formula I. The concentration corresponds to up to 100 g of active ingredient per hectare. Evaluation of the growth of the cereals is made 21 days after application. A comparison with untreated controls shows that the growth of cereal plants treated with compounds of formula I is reduced (60–90% of the controls) and that the diameter of the stalks has in some cases increased.

EXAMPLE B5

Growth inhibition of grasses

Seeds of the grasses *Lolium perenne, Poa pratensis, Festuca ovina, Dactylis glomerate* and *Cynodon dactylon* are sown in plastic dishes filled with an earth/peat/sand mixture (6:3:1), in a greenhouse, and watered as required. The emergent grasses are cut back weekly to a height of 4 cm, and about 50 days after sowing and 1 day after the last cut are sprayed with an aqueous spray mixture of a compound of formula I. The concentration of test compound corresponds to a rate of application of up to 100 g a.i. per hectare. The growth of the grasses is evaluated 21 days after application. The compounds of formula I effect a reduction in new growth in the range of 10–30% in comparison with untreated controls.

EXAMPLE B6

Preemergence test

In a greenhouse, seeds of the plants tested were sown in flower pots of 12–15 cm diameter. Immediately after sowing, the surface of the soil was treated with the aqueous dispersion of the compounds to be tested. Concentrations of 500, 125 and 30 g a.i./ha were employed. The pots were then kept in the greenhouse at 22°–25° C. and 50–70% relative humidity. The test was evaluated 3 weeks later in accordance with the following rating:
1: plants have not emerged or are totally withered
2–3: very pronounced action
4–6: medium action
7–8: weak action
9: no action (as untreated controls).

PREEMERGENCE ACTION

| Dosage in g a.i./ha | Compound No. 2.01 | | |
| --- | --- | --- | --- |
| plant tested | 500 | 125 | 30 |
| wheat | 5 | 8 | 9 |
| bromus tectorum | 1 | 2 | 5 |
| echinochloa crus galli | 2 | 4 | 8 |
| sorghum halepense | 2 | 3 | 8 |
| abutilon | 1 | 4 | 7 |
| chenopodium sp. | 1 | 2 | 4 |
| solanum nigrum | 2 | 3 | 4 |
| galium aparine | 2 | 2 | 3 |

What is claimed is:
1. A sulfonylurea of formula I

$$G-SO_2-NH-\overset{Z}{\overset{\|}{C}}-N-\overset{R^4}{\underset{}{}} \begin{matrix} N \diagup\!\!\!\!= \diagdown R^5 \\ E \\ N \diagup\!\!\!\!= \diagdown R^6 \end{matrix} \quad (I)$$

wherein
E is the methine bridge,
Z is oxygen or sulfur,
$R^4$ is hydrogen or $C_1$-$C_4$alkyl,
$R^5$ and $R^6$ are each independently hydrogen, halogen, $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_3$-$C_6$dialkoxyalkyl, $C_1$-$C_4$haloalkylthio, $C_2$-$C_4$-alkoxyalkyl, $C_3$-$C_6$-cycloalkyl or $-NR^{12}R^{13}$,
G is a group $R^1$ is hydrogen, halogen, nitro, $C_1$-$C_4$alkyl, $C_1$-$C_4$alkoxy, trifluoromethyl, trifluoromethoxy, difluoromethoxy, $C_1$-$C_4$alkyl carbonyl or $-COOR^{14}$,
$R^3$ is a group, n is 0, 1 or 2,
$R^8$ is hydrogen, $C_1$-$C_4$alkyl, $C_1$-$C_4$alkoxy, halogen, $C_1$-$C_4$haloalkyl, nitro, $-COOR^{14}$, $C_1$-$C_4$haloalkoxy, $-O-CR^{15}R^{16}-COOR^{14}$ or $-O-CR^{15}R^{16}-CN$,
$R^9$ is hydrogen, halogen, $C_1$-$C_4$alkyl, $C_1$-$C_4$alkoxy, $C_2$-$C_4$alkoxyalkyl oder $C_2$-$C_4$alkoxyalkoxy,
$R^{10}$ and $R^{11}$ are each independently hydrogen or $C_1$-$C_4$alkyl,
$R^{12}$ and $R^{13}$ are each independently hydrogen or $C_1$-$C_4$alkyl,
$R^{14}$ is hydrogen, $C_1$-$C_4$alkyl, $C_2$-$C_4$alkenyl, $C_3$-$C_4$alkynyl, or is $C_1$-$C_4$alkyl which is substituted by $C_1$-$C_4$alkoxy, halogen or phenyl, and
$R^{15}$ and $R^{16}$ are each independently hydrogen or $C_1$-$C_4$alkyl, or a salt thereof.
2. A compound according to claim 1, wherein Z is oxygen.
3. A compound according to claim 1, wherein $R^1$ is hydrogen, Cl, F, $CH_3$, $C_2H_5$, $CH_3O$, $CF_3$ or $CH_3CO$.
4. A compound according to claim 1, wherein $R^5$ and $R^6$ together contain not more than 4 carbon atoms and $R^4$ is hydrogen.
5. A compound according to claim 1, wherein G is 3-phenylpyridin-2-yl.
6. A compound according to claim 1, wherein Z is oxygen, $R^4$ is hydrogen and G is 3-phenylpyridin-2-yl and $R^5$ and $R^6$ together contain not more than 4 carbon atoms.
7. N-(3-Phenylpyridin-2-ylsulfonyl)-N'-(4,6-dimethoxypyrimidin-2-yl)urea according to claim 1.
8. A herbicidal and plant growth inhibiting composition which contains, as active ingredient, at least one substituted sulfonylurea of formula I according to claim 1, together with carriers and/or other adjuvants.
9. A method of controlling undesired plant growth, which method comprises applying to the plants or to the locus thereof an effective amount of a compound of formula I according to claim 1, or of a composition containing such a compound.

10. A method of inhibiting plant growth, which method comprises applying to the plants or to the locus thereof an effective amount of a compound of formula I according to claim 1, or of a composition containing such a compound.

11. A method of influencing plant growth for increasing yield, which method comprises applying to the plants or to the locus thereof an effective amount of a compound of formula I according to claim 1, or of a composition containing such a compound.

12. A method according to claim 9 of selectively controlling weeds pre- or postemergence in crops of useful plants.

13. A method according to claim 10 of suppressing plant growth beyond the 2-leaf stage, which method comprises applying the active ingredient preemergence.

14. A method according to claim 12, wherein the crops are rice crops.

* * * * *